United States Patent [19]

Henry et al.

[11] Patent Number: 5,358,490
[45] Date of Patent: Oct. 25, 1994

[54] APPARATUS FOR USE IN CENTRAL VEIN CANNULATION

[76] Inventors: Richard A. Henry, 7 Toronto Street, Kingston, Ontario K7L 4A3; Stevenson Shelley, 32 MacDonnell Street, Kingston, Ontario K7L 4B6, both of Canada

[21] Appl. No.: 81,197

[22] Filed: Jun. 25, 1993

[51] Int. Cl.⁵ .................................... A61M 5/178
[52] U.S. Cl. ......................... 604/167; 604/284
[58] Field of Search ........... 604/167, 247, 256, 272, 604/284; 137/846; 251/149

[56] References Cited

U.S. PATENT DOCUMENTS

| | | | |
|---|---|---|---|
| 4,143,853 | 3/1979 | Abramson | 132/846 |
| 4,387,879 | 6/1983 | Tauchinski | 137/846 |
| 4,535,819 | 8/1985 | Atkinson et al. | 604/247 |
| 4,935,008 | 6/1990 | Lewis, Jr. | 604/164 |
| 5,092,846 | 3/1992 | Nishijima et al. | 604/167 |
| 5,127,904 | 7/1992 | Loo et al. | 604/247 |

*Primary Examiner*—Jerome L. Kruter
*Attorney, Agent, or Firm*—Stanley E. Johnson

[57] ABSTRACT

Apparatus for central vein cannulation that includes a valved Y-connector for use between a conventional syringe and introducer needle. The valve is in an auxiliary arm and removably receives an end portion of a length of flexible tubing so that venous pressure can be visually observed during the medical procedure and then removed for insertion of a J-wire through the same valve by a conventional J-wire dispensing system.

8 Claims, 2 Drawing Sheets

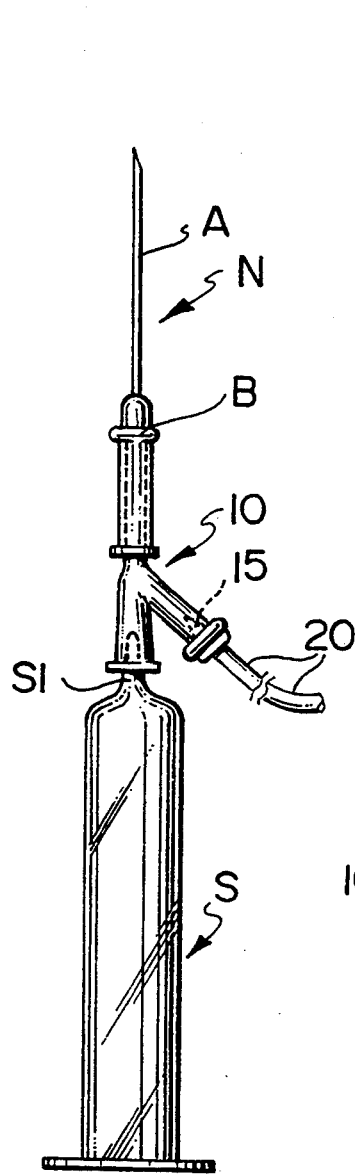
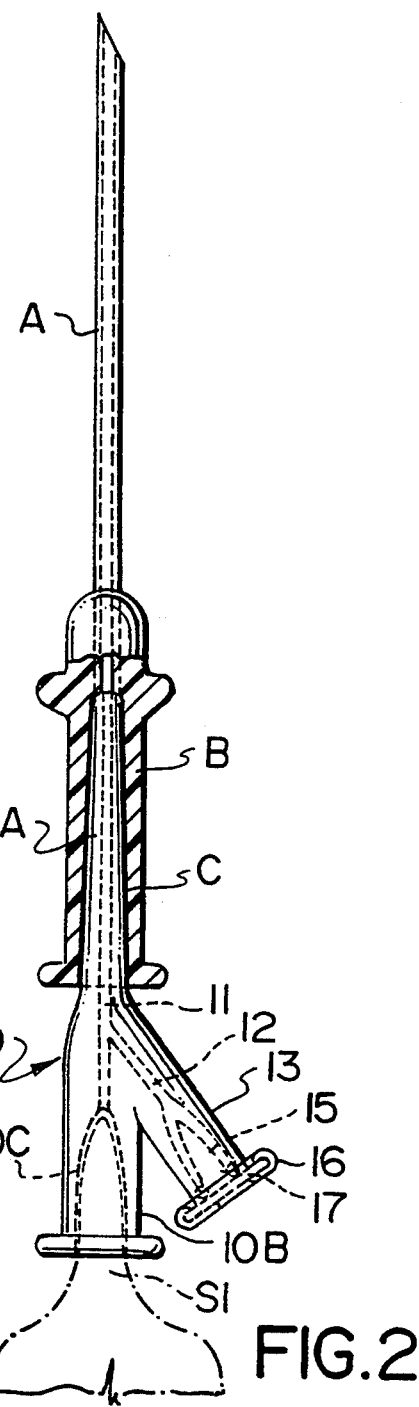
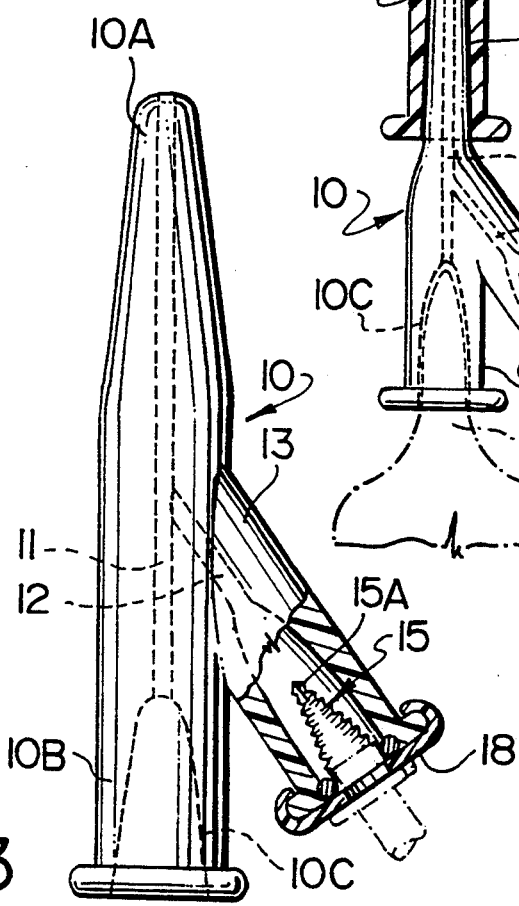
FIG.1
FIG.2
FIG.3

APPARATUS FOR USE IN CENTRAL VEIN CANNULATION

FIELD OF INVENTION

This invention relates generally to the field of medicine and more particularly to a valved Y-connector for use in blood vessel cannulation.

BACKGROUND OF INVENTION

Central venous catheters are used extensively in the care of critically ill patients. Insertion of these various forms of catheters is not risk free. The main problems with this procedure are inadvertent arterial puncture, air embolism, contamination with introduction of infection and spilling of blood onto the patient and/or medic. Arterial puncture (inadvertent and/or accidental) can result in significant morbidity; particularly if this is not recognized before large-bore catheters are introduced or infusion of solutions started. The incidence of arterial puncture in central vein cannulation procedures is reported to be about 2-15% confirming venous placement of the catheter is therefore important. A study has indicated there is a decrease in frequency of progression of inadvertent arterial puncture to arterial cannulation from 11.6% to 0% when a small-bore scouting needle is pressure transduced to confirm a venous pressure. It is thus important for the medic, especially in the operating room to have a reliable, quick and easy means of observing blood pressure of the vessel punctured. Conventionally X-ray confirmation of catheter placement is only done in the recovery room after the operation.

Two common systems currently available and in use for wiring are manufactured respectively by Arrow International Inc. and Baxter Healthcare Corporation. Neither system provides PVC tubing connection to allow hydrostatic manometry of the introducer needle. The 'Arrow Raulerson* Spring Wire Introduction Syringe' simplifies the technique of wiring the central vein but the benefits are only realised if manometry is not done. Disconnecting the syringe to attach an openended PVC manometer tube automatically negates the benefit of direct wiring through the attached syringe.

*Trade-Mark

To optimize the central vein cannulation technique the equipment should allow pressure transduction and wiring of the introducer needle without having to remove the syringe and open the system. Current techniques and methods do not allow the operator using the Seldinger technique of gaining venous access to pressure check the vessel and pass a guide wire into the vessel without removing the syringe and opening the introducer needle to the air. This results in blood loss onto the patient and hands of the operator thus contaminating the working area with blood. If the vessel has a negative pressure relative to atmospheric pressure air could be entrained into the needle into the vessel resulting in air embolism, which can be fatal.

Once the system is opened and in contact with the operator's hands, the risk of contamination is increased; this being more of a problem in the emergency situation where strict aseptic technique is difficult to achieve.

U.S. Pat. No. 4,935,008 issued Jun. 19, 1990 to R. L. Lewis Jr. discloses inserting a wire through one branch while leaving the syringe connected to another branch of a branched passage introducer needle. The patentee discloses an introducer needle for medical use consisting of a needle mounted in a hub and both of which are of special design. The needle has two lumens or passages one of which extends the entire length of the needle and hub and the other one of which extends along a major portion thereof but branches into an arm that has a valved passageway for introduction of a guide wire. The end of the syringe fits into the tapered cavity with a passage therefrom aligned with the first lumen or passage through the needle. The passageway is not valved in a manner to permit insertion of a tube for blood pressure measurement.

A separate Y-connector piece is disclosed in U.S. Pat. No. 4,998,977 issued Mar. 12, 1991 to D. Preise et al. The Y-connector piece detachably connects at one end to the hub of a puncturing cannula. A wire is fed into a blood vessel or artery through the main passage of the Y-connector and the branch passage detachably connects to a pressure measuring device.

U.S. Pat. No. 5,108,375 issued Apr. 28, 1992 to S. W. Harrison et al is directed to a closed system cannulating device and disclosed therein is a guide wire known as a J-wire commonly used in a cannulation procedure.

A Y-adaptor with a check valve is disclosed in U.S. Pat. No. 5,073,168 issued Dec. 17, 1991 to J. W. Danforth. A connector with a one way valve is disclosed in U.S. Pat. No. 4,842,591 issued Jun. 27, 1989 to R. B. Luther. A valved adaptor is also disclosed in U.S. Pat. No. 4,096,860 issued Jun. 27, 1978 to W. F. McLaughlin. A J-wire wire advancement system is disclosed in U.S. Pat. No. 4,917,094 issued Apr. 17, 1990 to A. S. Lynch and a modified adaptor is disclosed in U.S. Pat. No. 5,125,905 issued Jun. 30, 1992 to L. A. Wright et al.

The present invention is directed to an improvement over the teachings of the aforementioned U.S. Pat. Nos. 4,998,977 and 4,935,008. The latter patented structure is an integrated needle and hub with a complicated multiple passage needle structure in which the passages branch all of which contributes to high manufacturing cost. The teachings of U.S. Pat. No. 4,998,977 fails to provide a simplified pressure measuring system and wherein the pressure measurement and wire insertion utilize the same passageway leaving the other free for remaining attached to the syringe.

SUMMARY OF INVENTION

The disadvantages of the prior devices are overcome by the present invention wherein an individual valved connector piece is provided for use between a conventional introducer needle and a conventional syringe with a branch off the main passage being valved for alternate simple pressure measurement and guide wire insertion. The angle of the branch is such as to allow easy J-wire introduction using one hand while the other hand stabilizes the syringe.

The branched off passage is in a side arm of the device and the proximal end of such side arm is fitted with the valve. The valve is a latex one-way fish-mouth valve, or equivalent, that prevents backflow of blood while at the same time allows inserting thereinto an end portion of a length of PVC tubing. The PVC tubing through a vertical disposition thereof during use can visually indicate blood pressure or it can be connected or be connectable to a pressure gauge. The end of the tubing can be connected to the device before the needle is inserted into the vein or after blood has been aspirated.

Once a venous placement is confirmed the manometer tubing (aforementioned PVC tubing) is removed and the J-wire introduced through the same valved branch of the passage using a suitable guide wire advancement system as for example that disclosed in the aforementioned U.S. Pat. No. 4,917,094 or the equivalent. The J-wire can be introduced by inserting a Tuohy-Borst-type of adapter to pass the wire through the valve. The needle, connector and syringe are then removed as one, leaving the J wire in the blood vessel.

This system is superior to the prior systems (spring wire introduction syringe, double lumen introducing needle and closed system cannulating device) as it allows easy pressure confirmation of the vessel cannulated and spring wire introduction while maintaining a closed system and minimizing needle and syringe manipulation. This minimizes and/or reduces the risk of air embolism, contamination, blood spillage and most important of all makes pressure manometry of the vessel easy, safe and achievable in emergency situations with minimal extra equipment and skill. These features will greatly reduce the known risks associated with central venous catheter placement. The attachment is cheap to manufacture and is universally fitted to all needles and syringes making it useable in all hospitals world-wide with no change in current equipment needed other than the connector and a length of PVC tubing.

BRIEF DESCRIPTION OF THE DRAWINGS

The invention is illustrated by way of example in the accompanying drawing wherein:

FIG. 1 is a view of a conventional introducer needle, a conventional syringe and a valved Y-connector of the present invention interposed therebetween for use alternately in determining whether a vein or artery has been punctured with the needle and then introducing a guide wire into such vessel;

FIG. 2 is similar to FIG. 1 on a larger scale and in part section;

FIG. 3 is a view in part section of the valved Y-adaptor of FIGS. 1 and 2 on a larger scale;

DESCRIPTION OF PREFERRED EMBODIMENT

Figure 4:
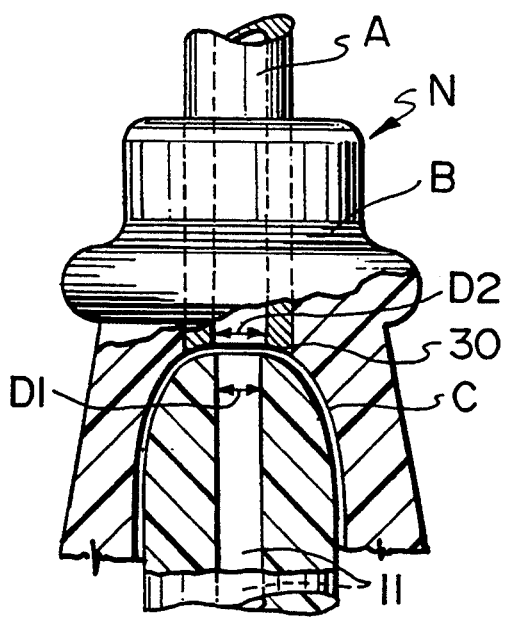
FIG. 4 is an enlarged view of a portion of FIG. 2.

Referring to FIG. 1 there is illustrated a conventional syringe S and a conventional introducer needle N that has a needle part A projecting from a housing or hub B which in turn has a socket C therein conventionally for receiving a distal end portion S1 of the syringe.

In accordance with the present invention there is provided a valved Y-connector piece 10 that has a branched passage consisting of a central through passage 11 (see FIGS. 2 and 3) and an auxiliary or branch passage 12 through a side arm 13. A membrane or cone type one way valve 15 projects into the passage 12 in the side arm 13 preventing out flow of liquid from such side arm.

The valve, by way of example, may be a conical accordion like body valve illustrated in FIGS. 2 and 3 with a normally closed slit 15A in the distal end or a valve similar to that illustrated in FIG. 3 of the aforementioned U.S. Pat. No. 5,073,168. The valve must be of the type that will removably receive an end portion of a PVC or the like tube 20 and which opens and sealingly closes respectively upon insertion and removal of the end of the tube.

The valve is retained in position in any convenient manner as for example by way of an end 16 of the valve 15 that stretches or rolls over an outwardly directed annular rib 17 on the end of the side arm as illustrated in FIG. 2 or by an annular end cap 18 snap press-fit onto such rib as illustrated in FIG. 3.

The main arm of the Y-connector device has a distal end 10A that sealingly fits into the socket C of the introducer needle and a proximal end 10B that has a socket 10C for sealingly receiving the distal end S1 of the syringe. The terms distal and proximal are used herein with distal being in reference to away from the medic toward the patient and proximal being away from the patient toward the medic when the apparatus is in use.

A length of PVC tubing 20 has an end portion 21 that is removably insertable into the valve 15 when the valve is in the arm 13. The depth of insertion is sufficient to open the valve and that depth of insertion is limited by an enlargement 22 on the tubing 20. When the introducer needle has been inserted into the patient the end 21 of the tubing 20 can be inserted into the valve and an immediate indication of pressure is observable by the vertical rise of blood in the tube and from which one immediately knows whether the needle struck a vein or an artery. Venous blood pressure is normally significantly lower than arterial pressure. Blood from a vein runs between 6 and 8 millimeters of mercury pressure above atmospheric pressure while from an artery it runs between 80 and 180 millimeters of mercury. Known pressure indicating means can be connected to tubing 20 if one so desires. With the introducer needle in the vein the PVC tubing is withdrawn from the side arm and the guide wire (J-wire) then fed progressively through the valve, the main channel 11 through the introducer needle and into the blood vessel.

Figure 5:
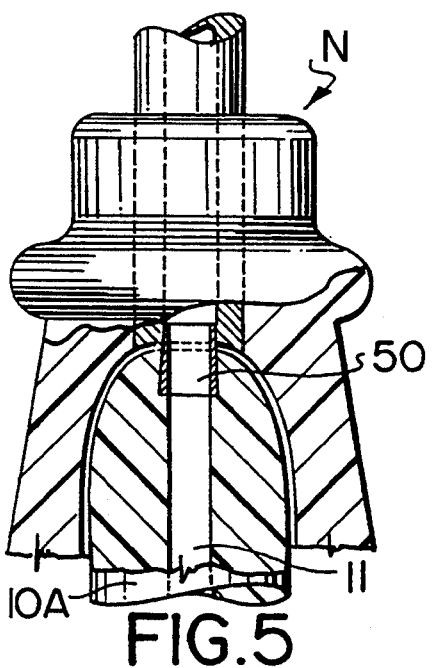
FIG. 5 is the same as FIG. 4 but illustrating a modification thereto.
Figure 6:
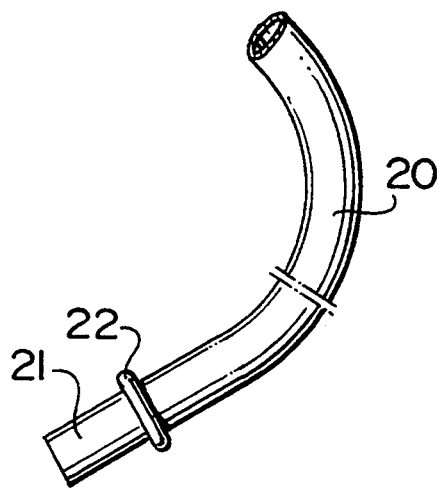
FIG. 6 is a view of an end portion of a PVC tubing.

The main channel 11 and/or the socket is designed such or has means preventing snagging of the leading end of the J-wire at the juncture of the Y-connector and the introducer needle as it is being fed therethrough. Effectively the design is such as to provide guide means for directing the end of the J-wire directly into the open end of the needle A. FIGS. 4 and 5 illustrate two different means for ensuring the guide wire passes smoothly from the connector 10 into the passage through the needle A.

Referring to FIG. 4, the distal end 10A of the connector 10 is illustrated as being in near proximity to the end 30 of needle A (preferably in abutting relation). In a structure where the end of the needle end is spaced from the base of the cavity then the distal end 10A should abut against the base of the cavity. Also in this latter instance the passage in the hub leading to the needle can taper decreasing in size in a direction toward the needle. Also the passage 11 through the connector is axially aligned with the passage through the needle and this is done through appropriate positioning of the passages, the socket C in the hub for the needle and by having the diameter D1 equal to or less than the diameter D2. In FIG. 5 a sleeve 50 is shown extending from the distal end 10A of the connector and projecting into the open end of the needle A. The sleeve 50 has at least an initial entry end (reference to feeding a guide wire into a patient's vessel) whose inner diameter is equal to that of or greater than the diameter of passage 11. The sleeve 50 is shown as a separate piece but it could be no more than a protruding tip formed integral with end 10A of piece 10 and projecting therefrom so as to project into the needle passage.

FIGS. 4 and 5 illustrate means to ensure the leading end of a guide wire (J-wire) doesn't snag at the junction of the Y-adaptor and the introducer needle. Other simple means of accomplishing the same will be obvious to those skilled in the manufacture of such articles.

Figure 7:
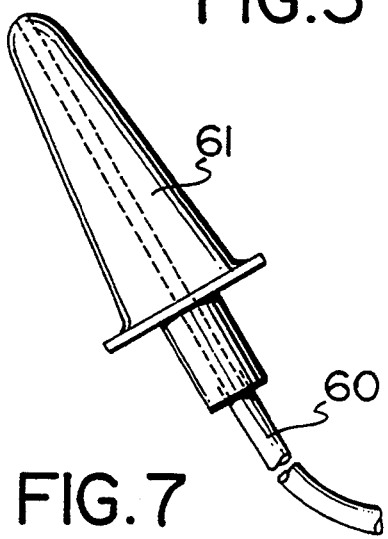
FIG. 7 illustrates an end portion of a J-wire with a sleeve on the end thereof keeping the J-wire straight.

In FIG. 7 there is illustrated an end portion of a conventional J-wire 60 and end straightener 61 disclosed more fully in the aforementioned U.S. Pat. No. 4,917,094 and/or 5,125,905. The wire end straightener 61 is insertable into valve 15 of the connector permitting easy passage of the J-wire therethrough.

We claim:

1. A device for use in central venous catheterization comprising a Y-connector having a main arm and a side arm as an integral unit, a main passage through said main arm and an auxiliary passage through said side arm, said auxiliary passage merging into said main passage and at a selected angle thereto, said main arm having a distal end sealingly insertable directly into a socket of an introducer needle and a proximal end, said proximal end having a cavity thereto sealingly to receive directly therein a nozzle end portion of a syringe, said main passage providing fluid flow communication between a passage through said introducer needle and said syringe, said auxiliary passage commencing at an open inlet end thereto and terminating at an end opposite thereto which merges into said main passage at a position between said syringe nozzle and said introducer needle, means, on at least one of a portion of said main passage adjacent said distal end and said socket of said introducer needle, to guide the leading end of a guide wire fed progressively through said auxiliary passage into a passage through the introducer needle and a one way valve means in said auxiliary passage at said open inlet end thereof, said one way valve having a normally closed opening therethrough preventing back flow of blood from said side arm during use of the device and permitting alternately removably inserting directly thereinto an end portion of a tube and a guide wire to be fed through said introducer needle.

2. A device as defined in claim 1 including means retaining said valve in said auxiliary passage.

3. A device as defined in claim 2 wherein said valve means has a normally closed slit at one end thereof providing said normally closed opening and an open ended cylindrical sleeve portion at the other end, wherein said side arm has a rib directed outwardly around the periphery thereof and wherein a portion of the open end of the valve is rolled over said rib thereby providing said valve retaining means.

4. A device as defined in claim 2 wherein said means comprises an annular cap snap-fit onto said auxiliary arm and with an outer rim portion of said valve being held captive between such cap and said side arm circumscribing entry into said auxiliary passage.

5. A device as defined in claim 1 wherein said valve has a main body portion that is generally conical in form providing a tapering cavity to receive therein said tube end portion, said valve having a slit at the end of the conical cavity providing said opening through.

6. Apparatus for use in central venous catheterization comprising a Y-connector having a main arm and a side arm as an integral unit, a main passage through said main arm and an auxiliary passage through said side arm, said auxiliary passage merging into said main passage and at a selected angle thereto, said main arm having a distal end sealingly insertable directly into a socket of an introducer needle and a proximal end, said proximal end having a cavity therein sealingly to receive directly therein a nozzle end portion of a syringe, said main passage providing fluid flow communication between a passage through said introducer needle and said syringe, said auxiliary passage commencing at an open inlet end thereto and terminating at an end opposite thereto which merges into said main passage at a position between said syringe nozzle and said introducer needle, means, on at least one of a portion of said main passage adjacent said distal end and said socket of said introducer needle, to guide the leading end of a guide wire fed progressively through said auxiliary passage into a passage through the introducer needle and a one way valve means in said auxiliary passage at said open inlet end thereof, said one way valve having a normally closed opening therethrough preventing back flow of blood, during use, from said side arm and permitting alternately removably inserting directly thereinto an end portion of a tube and a guide wire to be fed through said introducer needle and a length of flexible tubing for use therewith, said tubing having means thereon to limit the depth of penetration of an end portion thereof into said valve.

7. Apparatus as defined in claim 6 wherein said tubing is open at each of its opposite ends.

8. Apparatus as defined in claim 7 wherein said tubing is PVC.

* * * * *